United States Patent [19]
Singer

[11] Patent Number: 5,318,682
[45] Date of Patent: Jun. 7, 1994

[54] SAMPLE-WELL FORMING COMB FOR HORIZONTAL GEL ELECTROPHORESIS DEVICE

[75] Inventor: Paul A. Singer, Del Mar, Calif.

[73] Assignee: GenSura Laboratories, Inc., Del Mar, Calif.

[21] Appl. No.: 118,008

[22] Filed: Sep. 8, 1993

[51] Int. Cl.⁵ ................... G01N 27/26; G01N 27/447
[52] U.S. Cl. ............................. 204/182.8; 204/180.1; 204/299 R
[58] Field of Search ............. 204/182.8, 299 R, 180.1

[56]  References Cited

U.S. PATENT DOCUMENTS

| | | | |
|---|---|---|---|
| 4,234,400 | 11/1980 | Kaplan et al. | 204/182.8 |
| 4,294,684 | 10/1981 | Serwer | 204/182.8 X |
| 4,415,418 | 11/1983 | Turre et al. | 204/299 R X |
| 4,883,577 | 11/1989 | Sugimoto et al. | 204/299 R |
| 4,889,610 | 12/1989 | Flesher et al. | 204/182.8 X |
| 5,164,065 | 11/1992 | Bettencourt et al. | 204/299 R |
| 5,232,573 | 8/1993 | Rosenvold | 204/182.8 X |

FOREIGN PATENT DOCUMENTS

| | | | |
|---|---|---|---|
| 63-259455 | 2/1988 | Japan | 204/299 R |
| 63-47648 | 11/1988 | Japan | 204/299 R |
| 9300583 | 1/1993 | PCT Int'l Appl. | 204/299 R |

*Primary Examiner*—John Niebling
*Assistant Examiner*—John S. Starsiak, Jr.
*Attorney, Agent, or Firm*—Spensley Horn Jubas & Lubitz

[57]  ABSTRACT

A gel displacement comb and method for using the same to form multiple sample-wells on a gel within a horizontal electrophoresis device are disclosed. The comb comprises a base and a plurality of regularly spaced teeth projecting linearly from the base, the teeth being essentially of trapezoidal shape, separated by triangular spaces having a pointed apex such that the height H of the triangular space and the width B of the base of the triangle space satisfy the following equations:

$$H = T - D, \quad B < \tfrac{1}{2} H$$

wherein T represents the thickness of the gel and D represents a predetermined distance between the bottom of the gel and the end of the teeth when the comb is inserted in the electrophoresis device.

8 Claims, 4 Drawing Sheets

SAMPLE-WELL FORMING COMB FOR HORIZONTAL GEL ELECTROPHORESIS DEVICE

BACKGROUND OF THE INVENTION

1. Field of the Invention

This invention relates to electrophoresis devices, and more particularly, to a novel gel displacement type comb for such devices.

2. Description of Related Art

Electrophoresis is a technique that is currently used in the separation of proteins, lipoproteins, DNA, and RNA. This technique involves the separation of charged macromolecules due to their differential mobilities through a porous gel under an applied electric field. Commonly used gels are polyacrylamide and agarose.

Usually, electrophoresis separation can be based on differences in molecular weight, and is a particularly powerful tool for separation or fractionation of macromolecule mixtures in which the molecular weights of the molecules are from about 10,000 to about 10 million or more daltons.

Gel electrophoresis devices may be classified into two general types: vertical and horizontal. Both types have been well documented in the literature.

For the application of samples for gel electrophoresis, a sample well-forming device (commonly referred to as a "comb") is used. As illustrated in FIG. 1, a standard comb 10 is generally of a rectangular shape, from 2 to 5 cm in width and 5 to 20 cm in length, and flattened (from 0.2 mm to 2 or 3 mm thick), having along one long side a plurality of rectangular shaped protrusions (or "teeth") 12, each being of about 2.5 to 10 mm or more in width, separated by generally narrower (i.e., 1.6-3 mm) rectangular indentions 13 (or spaces). The standard comb is made of a plastic material. Delrin (or acetal), lexan, and acrylic, among others, have been used as the plastic material. In one common form of prior art applicable to both vertical and horizontal gel formats, such combs are inserted into the still liquid gel medium, which flows into the spaces between the teeth and then solidifies. When the comb is removed, a void is left in the gel matrix in the place where the teeth had excluded the liquid gel medium. This void is referred to as the "sample well."

Vertical and horizontal gels differ in the relationship of the comb, the sample wells, and the direction with respect to these that the sample travels during electrophoresis. Vertical gels are formed between two rectangular glass plates separated by a spacer of a given thickness (0.2 mm to 3 mm or slightly more, and nominally equal to the thickness of the comb) which commonly has three closed (and sealed) sides and one open side. The gel material is poured into the open side, filling the space between the plates to within a few mm of the edge of the open side. The comb is then introduced between the plates at the open side and pushed down into the liquid gel until its teeth become at least partially, or more commonly, completely submerged in the liquid gel medium.

Upon removal of the comb from the solidified gel medium, rectangular shaped voids (wells) are left at the edge of the gel. Such voids are delineated at the front and rear by the front and rear glass plates respectively, and at the sides and bottom by the solidified gel medium itself. "Fingers" of solidified gel medium (also referred to as "well dividers") formed from liquid gel that flowed into spaces between the comb teeth serve to separate the sample wells from each other. When electric current is applied, the sample migrates parallel to the plane of the comb (now removed), toward the floor of the vertical well, and from there through the length of the gel medium, toward the cathode.

In horizontal gels, the liquid gel (most often agarose) is poured to a given thickness (usually 4 to 5 mm) onto a horizontal, flat, rectangular plate, bounded on all four sides by walls which serve to contain the gel medium (i.e., a "tray"). The comb is orientated perpendicular to the plane of the horizontal gel, near one side of the gel (which will become the anodic side during electrophoresis), and held firmly in place with the bottom of the teeth suspended approximately 1 mm above the base of the tray, usually supported by the side walls of the tray using a bridging device. The liquid gel medium flows around the teeth and into the spaces between the teeth and solidifies. Upon removal of the comb, voids are left in the gel as sample wells, which are delineated entirely by gel medium—on both broad faces, the floor and the two sides. Wells are separated from one another by the solidified gel medium which occupied the spaces between the teeth of the comb. During electrophoresis, samples migrate perpendicular to the plane of the comb, exiting the broad face of the well on the cathodic side and migrating through the gel medium towards the cathode.

A significant shortcoming of the prior art relative to the introduction of sample wells into vertical and horizontal gel formats is the limited proximity of adjacent wells that can be achieved with conventional combs. Maximum proximity is desirable since it affords a more accurate comparison of the mobilities of samples in neighboring lanes, and allows more sample wells of any particular width to be accommodated within a gel of given overall width. This problem arises with conventional combs because to assure the structural integrity of the well, a given minimum thickness of gel medium must be provided to divide individual wells. This is particularly true given that both polyacrylamide and (particularly) agarose gel matrices posses rather limited structural strength. The problem is further exacerbated by the stress forces placed upon the fragile gel dividers through the necessary action of removing the comb from the solidified gel. This stress derives from the frictional drag of the comb in contact with the gel and the partial vacuum generated upon removal of the comb, since adhesion of the gel to the comb hinders pressure equalization by blocking the inflow of air into the well.

In the case of vertical polyacrylamide gels, this shortcoming has been addressed and eliminated by the use of a comb which functions using a substantially different principle from that of the conventional gel displacement combs described above. This comb, called the "sharkstooth" comb (devices of U.S. Pat. Nos. 4,883,577 and 5,164,065) consists of sharply pointed teeth which are pressed firmly against the already solidified edge of the gel medium (exclusively polyacrylamide) sandwiched between two glass plates. The spaces between the teeth are not allowed to pushed completely between the glass plates, but are rather allowed to extend above the plate. This allows access for sample loading through the open side of the sandwiched plates, to the spaces above the gel surface, which corresponds to the spaces between the comb's teeth. Such spaces are delineated on each side by the edges of adjacent teeth and on the bottom by the surface edge of the gel medium. Thus, in this case, it is the spaces between the teeth, rather than gel medium displaced by the body of the teeth, which form the sample wells.

Unlike gel displacement combs, the sharkstooth comb is not withdrawn since this would negate its well-forming function, but rather stays in place during sample loading and at least until all sample has entered the gel matrix. Since the sharksteeth narrow to a point (where the points of the teeth make contact with the gel surface), adjacent lanes are formed in close proximity (essentially touching).

Importantly, the sharkstooth principle cannot be used with horizontal gels since horizontal gel formats of necessity require gel displacement type wells to be formed. Until now, no attempt has been made to bring the same advantages of close proximity wells to the horizontal gel format using a gel displacement comb. The present invention addresses this need by providing novel geometry of the teeth of a gel displacement type comb for horizontal gel electrophoresis.

SUMMARY OF THE INVENTION

In view of the foregoing, it is an object of the present invention to provide a novel gel replacement type comb capable of forming a multiplicity of sample wells with close proximity hitherto unachievable by a conventional comb in a gel bed within a horizontal gel electrophoresis device.

It is another object of the present invention to provide a gel displacement type comb for perpendicular insertion in a horizontal electrophoresis device, the comb comprising a base and a plurality of regularly spaced teeth projecting linearly from the base, the teeth being essentially of trapezoidal shape, separated by triangular spaces having a pointed apex such that the height H of the triangular space and the width B of the base of the triangular space satisfy the following equations:

$$H = T - D \quad B < \tfrac{1}{2} H$$

wherein T represents the thickness of the gel and D represents a predetermined distance between the bottom of the gel and the end of the teeth when the comb is inserted in the electrophoresis device.

It is still further object of the present invention to provide a method of forming sample wells in a gel bed for use in a horizontal electrophoresis, the method comprising the steps of:

(a) providing an electrophoresis gel tray and a gel displacement type comb for perpendicular insertion in a horizontal electrophoresis device, the comb comprising a base and a plurality of regularly spaced teeth projecting linearly from the base, the teeth being essentially of trapezoidal shape, separated by triangular spaces having a pointed apex such that the height H of the triangular space and the width B of the base of the triangular space satisfy the following equations:

$$H = T - D \quad B < \tfrac{1}{2} H$$

wherein T represents the thickness of the gel and D represents a predetermined distance between the bottom of the gel and the end of the teeth when the comb is inserted in the electrophoresis device;

(b) inserting the gel displacement type comb perpendicularly to the tray along the anodic end of the gel to be formed such that the comb is in a fixed position and the ends of the teeth are spaced at the predetermined distance D from the floor of the tray;

(c) pouring liquified gel into the tray such that the surface level of the gel is essentially at the pointed apex of the triangle spaces of the comb; and (d) removing the comb from the gel bed after solidification of the gel to obtain a multiplicity of sample-wells cast in the solidified gel.

The above objects, as well as further objects, features and advantages of the present invention, will be more fully understood by reference to the following detailed description and the accompanying drawings.

BRIEF DESCRIPTION OF THE DRAWINGS

Like numbers in the drawings refers to like elements.

DETAILED DESCRIPTION OF THE INVENTION

Figure 1:
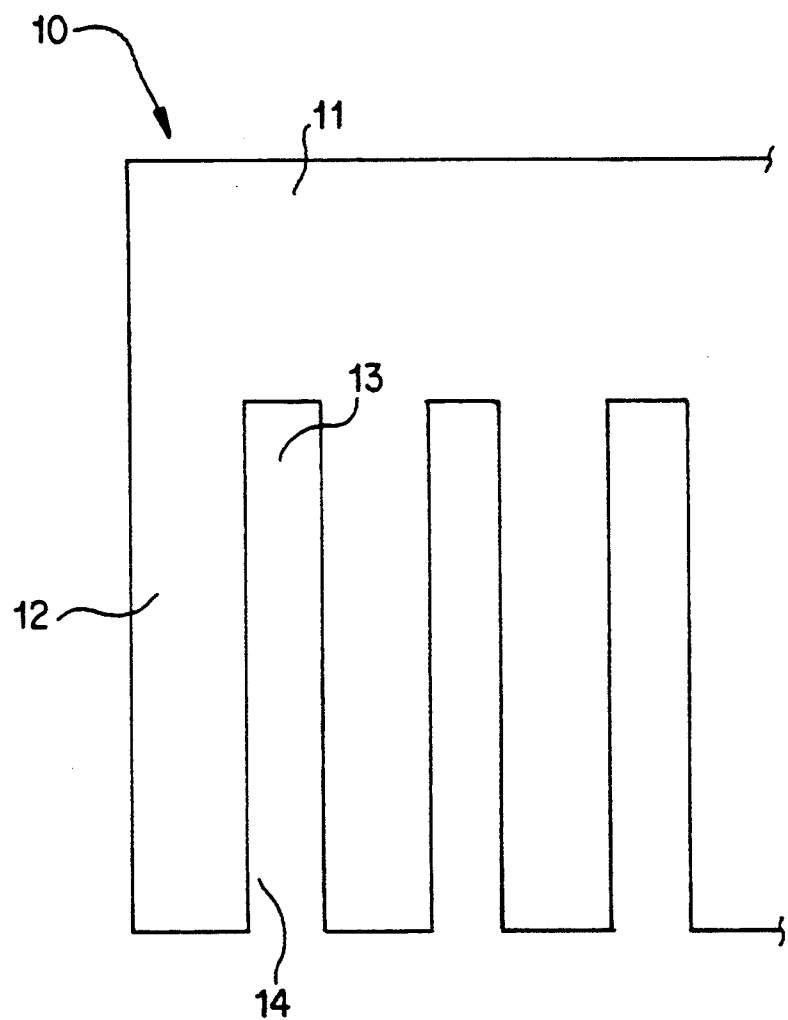
FIG. 1 is a partial enlarged side elevation view of a prior art comb.
Figure 2:
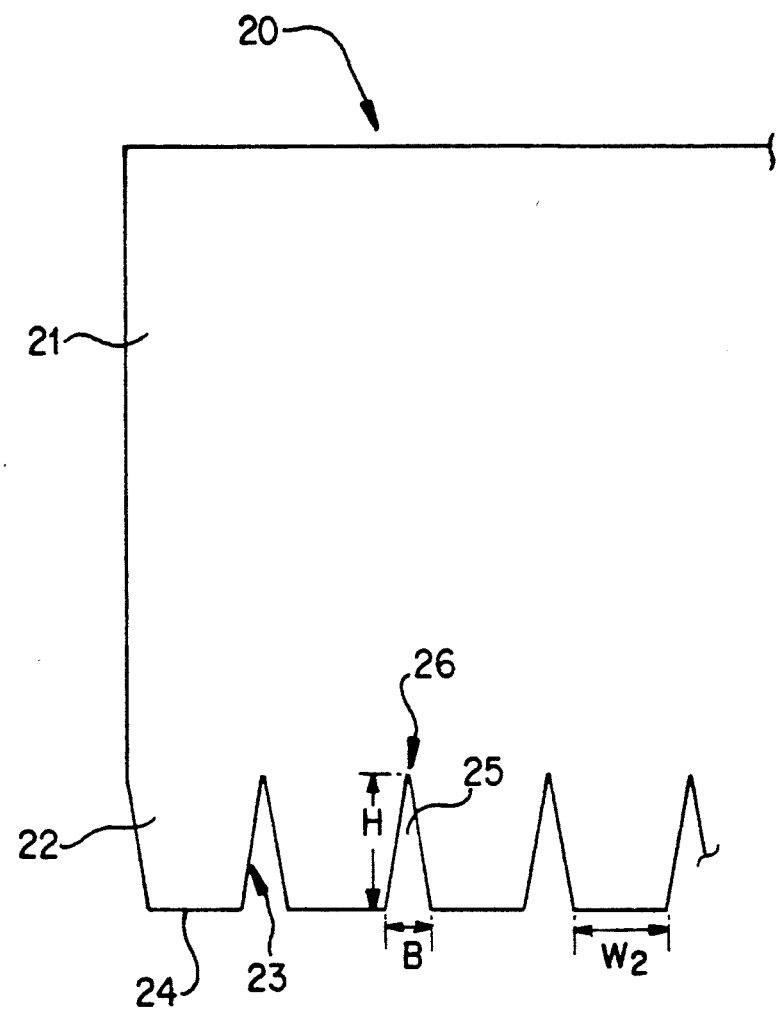
FIG. 2 is a partial enlarged side elevation view of an embodiment of the comb in accordance with the present invention.

According to the present invention, a gel displacement type comb has been designed for use with the horizontal gel format which provides for the effective narrowing of the spaces between the wells, bringing the associated advantages—i.e., close proximity of lanes for more accurate side-by side mobility comparison and more lanes per given gel width—to this gel format for the first time. Referring to FIG. 2, there is shown an embodiment of a gel displacement type comb 20 in accordance with the present invention. The comb 20 can be generally of rectangular shape, from 2–5 cm in width, 5–20 cm in length, and flattened (from 0.2 to 3 mm thick, preferably 0.8–1.5 mm), having a plurality of teeth. Structurally, the comb 20 comprises a base 21 and a plurality of teeth 22. The teeth are regularly spaced longitudinally along the base 21. Each tooth 22 is of essentially trapezoidal shape, wider at the top and narrower at the bottom, and parallel to each other. Between two adjoining teeth, a space 25 of essentially triangular shape having a pointed apex 26 at the top and widening to the base thereof is provided.

The height of the triangle space "H", also measured as the depth of the teeth 22 is crucial to the present invention. The "H" is set to coincide with the thickness "T" of the gel to be formed minus a predetermined distance "D". The "D" is a desirable space to be left between the ends 24 of the teeth and the surface of a gel tray (or the bottom of the gel) on which the gel is to be poured when the comb is in place. Such space is required to allow for the liquid gel to form a floor for the sample well. Thus, "H" is defined by the equation H=T−D. Preferably, "D" is about 1 mm. The gel thickness "T" is generally in the range of 4 to 5 mm, that found for use in standard horizontal analytical agarose gels. Therefore, the preferred height "H" is from about 3 to 4 mm. This preferred range contrast with the tooth depth in conventional combs, which bears no relation to the thickness of the gel.

Another essential feature of the present invention is that the triangular space 25 be as narrow as practical at its base, thereby augmenting the overall desirable effect of reducing the effective space between the wells. Practically, the width "B" of the base of the triangle space 25 should not be greater than a half of the triangle height "H". Thus, "B" is defined by the equation B<½H. Preferably, "B" is from about 0.5 to about 2.0 mm, more preferably from about 1.0 to about 1.6 mm. As will be discussed below, "B" can be significantly narrower than that found in standard combs. The base width "B" of standard combs is rarely reduced below 1.6 or 1.8 mm, as thinner "fingers" of agarose would be too weak and subject to breakage.

The teeth 22 have slanted sides 23. The degree of slope of the sides is determined by the chosen base width "B" and triangle spaced height "H" for a given embodiment. This can also be expressed by the ratio, H:B, and is typically in the range of 2-3:1. For example, in a 3 mm "H", a 1 mm, 1.2 mm and 1.5 mm "B" would correspond to a 3:1, 2.5:1, and 2:1 ratio, respectively. These values represent those typical for the preferred embodiment. For a 4 mm "H", a 1.33 mm, 1.6 mm, and 2.0 mm "B" would be the corresponding values for the above ratios. These ratios will be translated into approximately 9.5, 11 and 14 degrees off the vertical. Thus, the preferred angle of the slope would be from about 9 to about 15 degrees. The most preferred embodiment has such dimensions as H:B=4 mm:1.6 mm or 3 mm: 1.2 mm. The width "W2" of the teeth 22 is preferably from about 2 mm to 10 mm, which is not substantially different from that found in conventional combs.

The mode of operation of the comb 20 is essentially the same as that for the prior art comb 10. Thus, the comb 20 of the present invention is operationally in place in a gel tray by being suspended such that the end 24 of the teeth 24 is distanced by the predetermined "D", approximately 1 mm above the base of the tray. After the comb 20 has been inserted in the tray near one side which corresponds to the anodic end of the gel to be formed and firmly held in position, liquified agarose gel is poured into the gel tray. Due care should be taken so that the surface level of the gel reach precisely the apex 26 or its vicinity. After allowing the agarose gel to harden for a sufficient period of time, the comb is removed from the gel by slowly pulling in a vertical direction. Removal of the comb 20 leaves a plurality of sample-wells aligned longitudinally along the anodic side of the gel.

The gel is overlayed with electrophoresis buffer, and the sample aliquots are loaded into the sample-wells formed by the teeth of the gel displacement type comb of the present invention. Electrophoresis is conducted in a conventional manner.

A major advantage of the comb 20 over the prior art combs such as comb 10 is that more numbers of sample-wells can be cast within a given gel width, since less space is required between the wells, and that the comb 20 allows neighboring lanes to be as close as desired for accurate band comparison. This is made possible because the triangular well dividers, formed by the solidified agarose in the triangular space 25 reaches its apex precisely or very near the gel surface, and thus reduce the effective spacing between the wells. It should be noted that having the apex beneath the surface of the gel (i.e., H<T−D) offers no improvement, since the samples can only be loaded as high as the divider apex without flowing into neighboring wells. Another advantage is that the comb 20 significantly reduces the stress placed upon the well dividers upon comb removal, since the upward motion of the comb allows the sides 23 of the teeth to pull away from the sloped walls of the well it has formed. This essentially eliminates the friction between the tooth sides 23 and well sides, and allows the well to equilibrate much more efficiently with air pressure than with the conventional comb design. In contrast, the straight sides 13 of the comb 10 adhere to the gel floor of the well and create a partial vacuum as the comb is removed, thereby pulling up the gel and often destroying it. Because of the stress reduction, the narrowing of the base width can be achieved according to the present invention. This, in turn, also contributes to reduction of the effective well spacing.

Figure 3:
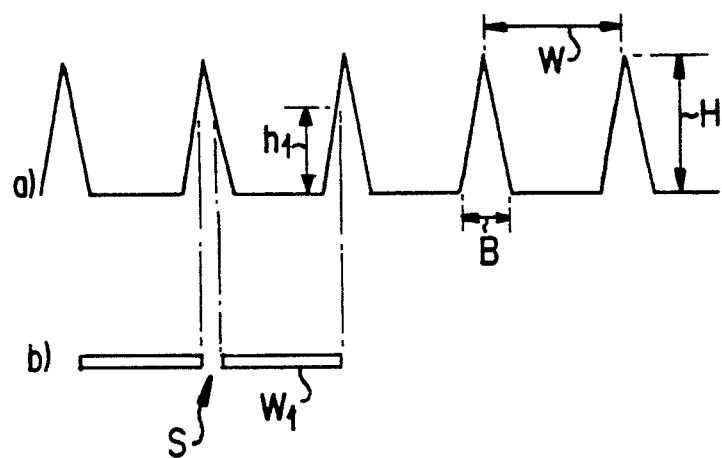
FIGS. 3a and 3b are an illustrative side view of the teeth of the comb described in FIG. 2 in relation to sample bands developed after electrophoresis.
Figure 4:
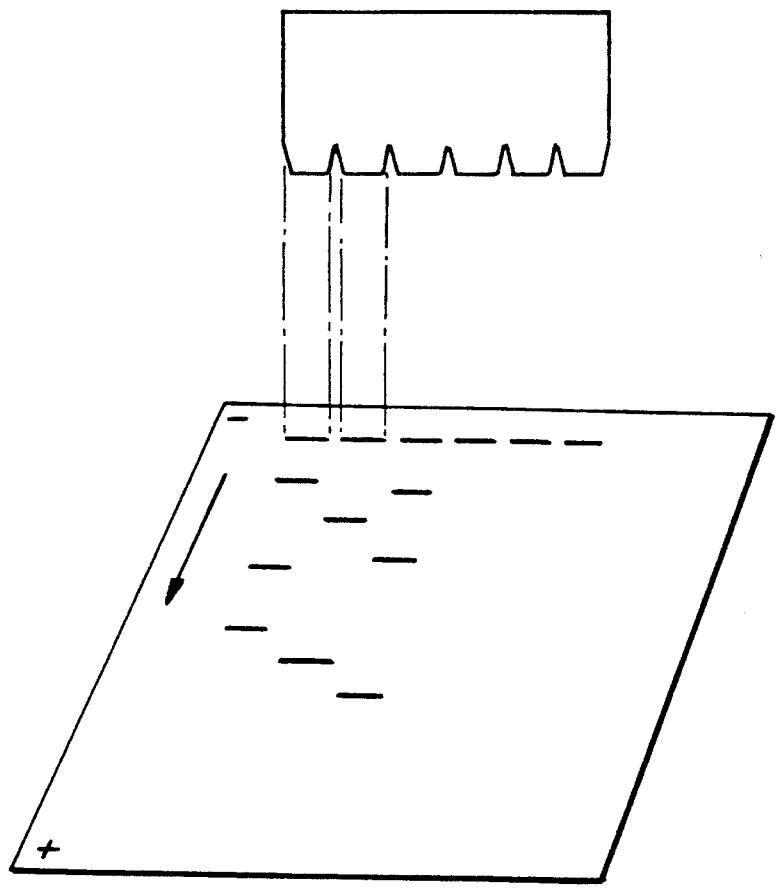
FIG. 4 is a perspective view of the comb described in FIG. 2 as it would produce sample-wells and the corresponding bands.

Referring now to FIGS. 3a, 3b, and 4, a side and a perspective view of the comb 20 are presented in relation to sample bands 30 (e.g., DNA, RNA, or protein) which would be formed after electrophoresis. These FIGS., in particular FIG. 3a and 3b, depict the apparent separation of the sample wells, i.e., the reduction of same, achieved with the combs according to the present invention.

In FIG. 3a, the apparent band width w1 is given by: w1=w−s, where w is the width of each tooth at its upper side (or the distance from apex to apex of adjacent triangular spaces), and s is the apparent separation of the wells, as determined by the apparent separation of visible sample bands electrophoresed from the wells and visualized by dye staining, in the usual manner from a perspective directly above and perpendicular to the flat plane of the gel. The value of s, which represents the measure of the effective reduction of the space between the wells, depends on the base width B, the height (H) of the triangular space, and some value (h1) which is a function of the height of the loaded sample, and the strength of the detectable sample signal. It can be appreciated that the sample signal strength must be factored into this calculation since, when viewed from above, the amount of sample material directly above the sloping side of the well is proportionally less than that amount of sample material directly above the floor of the well. This value, h1, is empirically determined; however a typical value for the preferred embodiment of the invention is found to be ⅓−⅔H (in FIG. 3 it is shown as ⅔H). That is, the sample signal is sufficiently strong, and the sample loaded high enough in the well such that all sample below the ⅔ level in the well is detectable. The value of s is thus given by:

$$s=(H-h1/H)B$$

In FIG. 3, where H=3 mm, h1=2 mm, and B=1.2 mm $$s=0.4 \text{ mm}$$

Thus, in this example, 0.4 mm effective well spacing is achieved with the comb of the present invention, compared with the typical best value of 1.6 mm achievable with conventional gel displacement combs for horizontal gel electrophoresis.

The following table indicates typical percentage spacing achievable with a preferred embodiment of the invention in which the H:B ratio of the triangular space between each tooth is 2.5:1, the H is 3.0 mm, and the value or h1 is taken to be $\frac{2}{3}H$ (or 2.00 mm). Comparison is made with conventional combs for several tooth widths. In each case, the effective tooth width (or lane width) of the comb of the present invention (wl) is compared with the equivalent tooth (and lane) width of a conventional comb having fixed 1.6 mm spacing between teeth.

| INVENTION COMB | | | | STANDARD COMB | | | Space savings with Invention Comb |
| --- | --- | --- | --- | --- | --- | --- | --- |
| Nominal tooth width | Effective lane width | Effective lane width | Width of 10 lanes | Tooth (and lane) width | Teeth (and lane) spacing | Width of 10 lanes | |
| 3.0 mm | 2.6 mm | 0.4 mm | 30.0 mm | 2.6 mm | 1.6 mm | 42.0 mm | 28.6% |
| 3.5 mm | 3.1 mm | 0.4 mm | 35.0 mm | 3.1 mm | 1.6 mm | 47.0 mm | 25.5% |
| 4.0 mm | 3.6 mm | 0.4 mm | 40.0 mm | 3.6 mm | 1.6 mm | 52.0 mm | 23.1% |
| 4.5 mm | 4.1 mm | 0.4 mm | 45.0 mm | 4.1 mm | 1.6 mm | 57.0 mm | 21.0% |
| 5.0 mm | 4.6 mm | 0.4 mm | 50.0 mm | 4.6 mm | 1.6 mm | 62.0 mm | 19.4% |

While preferred specific embodiments of the present invention are hereinabove set forth, it should be realized that many alternatives, modifications and variations will be apparent to those skilled in the art of the foregoing description and therefore that the invention is not to be limited to the exact design and constructions illustrated and described therein. Accordingly, the scope of the invention should be determined not by the embodiments detailed but by the appended claims and their legal equivalents.

I claim:

1. A gel displacement type comb for perpendicular insertion in a horizontal electrophoresis device, the comb comprising a base and a plurality of regularly spaced teeth projecting linearly from the base, the teeth being essentially of trapezoidal shape, separated by triangular spaces having a pointed apex such that the height H of the triangular space and of the width B of the base of the triangle space satisfy the following equations:

$$H = T - D, \quad B < \tfrac{1}{3}H.$$

wherein T represents the thickness of the gel and D represents a predetermined distance between the bottom of the gel and the end of the teeth when the comb is inserted in the electrophoresis device.

2. The gel displacement type comb according to claim 1, wherein the predetermined distance D is about 1 mm.

3. The gel displacement type comb according to claim 1, wherein the gel thickness T is from about 4 to about 5 mm.

4. The gel displacement type comb according to claim 1, wherein the height H is from about 3 to about 4 mm.

5. The gel displacement type comb according to claim 1, wherein the base width B is about 0.5 to about 2 mm.

6. The gel displacement type comb according to claim 1, wherein the width of the teeth $W_2$ is from about 2 to about 10 mm.

7. The gel displacement type comb according to claim 1, wherein the sides of the teeth form a angle of from about 9.0 to about 14.0 degrees off vertical.

8. A method of forming sample wells in a gel for use in a horizontal electrophoresis, the method comprising the steps of:

(a) providing an electrophoresis gel tray and a gel displacement type comb for perpendicular insertion in a horizontal electrophoresis device, the comb comprising a base and a plurality of regularly spaced teeth projecting linearly from the base, the teeth being essentially of trapezoidal shape, separated by triangular spaces having a pointed apex such that the height H of the triangular space and the width B of the base of the triangle space satisfy the following equations:

$$H = T - D \quad B < \tfrac{1}{3}H$$

wherein T represents the thickness of the gel and D represents a predetermined distance between the bottom of the gel and the end of the teeth when the comb is inserted in the electrophoresis device;

(b) inserting the gel displacement type comb perpendicularly to the tray along the anodic end of the gel to be formed such that the comb is in a fixed position and the ends of the teeth are spaced at the predetermined distance D from the floor of the tray;

(c) pouring liquified gel into the tray such that the surface level of the gel is essentially at the pointed apex of the triangle spaces of the comb; and (d) removing the comb from the gel bed after solidification of the gel to obtain a multiplicity of sample-wells cast in the solidified gel.

* * * * *